United States Patent [19]

Porteous

[11] Patent Number: 4,489,235
[45] Date of Patent: Dec. 18, 1984

[54] HYDROCOLLOID CONDITIONER APPARATUS

[76] Inventor: Don D. Porteous, 8894 Regent St., Los Angeles, Calif. 90034

[21] Appl. No.: 579,478

[22] Filed: Feb. 13, 1984

[51] Int. Cl.³ .............................................. F27D 11/00
[52] U.S. Cl. ..................................... 219/437; 99/333; 219/329; 219/417; 219/419; 219/441; 219/428; 219/478; 219/494; 422/292
[58] Field of Search ............... 219/415, 417, 419, 428, 219/432, 435, 436, 437, 441, 442, 494, 478, 521, 523; 422/292, 243, 307, 308; 99/333; 106/35, 38.2

[56] References Cited

U.S. PATENT DOCUMENTS

| | | | |
|---|---|---|---|
| Re. 29,609 | 4/1978 | Wadia et al. | 219/494 |
| 2,778,920 | 1/1957 | Pavelka, Jr. | 219/437 |
| 2,805,314 | 9/1957 | Michaelis | 219/437 |
| 2,851,576 | 9/1958 | Ripley | 219/415 |
| 3,345,497 | 10/1967 | Porteous | 219/417 |
| 3,801,278 | 4/1974 | Wagner et al. | 219/417 X |
| 4,192,992 | 3/1980 | Stevens et al. | 219/494 |

FOREIGN PATENT DOCUMENTS 404822 7/1966 Switzerland ...................... 219/437

Primary Examiner—Volodymyr Y. Mayewsky
Attorney, Agent, or Firm—Wagner & Bachand

[57] ABSTRACT

A microprocessor controlled hydrocolloid conditioner comprising a frame, a bath tank separably supported by said frame for containing water heated to a pre-determined temperature useful in the conditioning of hydrocolloid material, heating means comprising a power supply and a heating element disposed within the bath, and a microprocessor interfaced with a triac control circuit for turning on and off the heating means responsive to command from the microprocessor such that boiling cycles are automatically commenced and terminated, holding and tempering baths are readily set and the dentist is signalled the status and readiness of hydrocolloid at all times in each of multiple function bath tanks.

19 Claims, 7 Drawing Figures

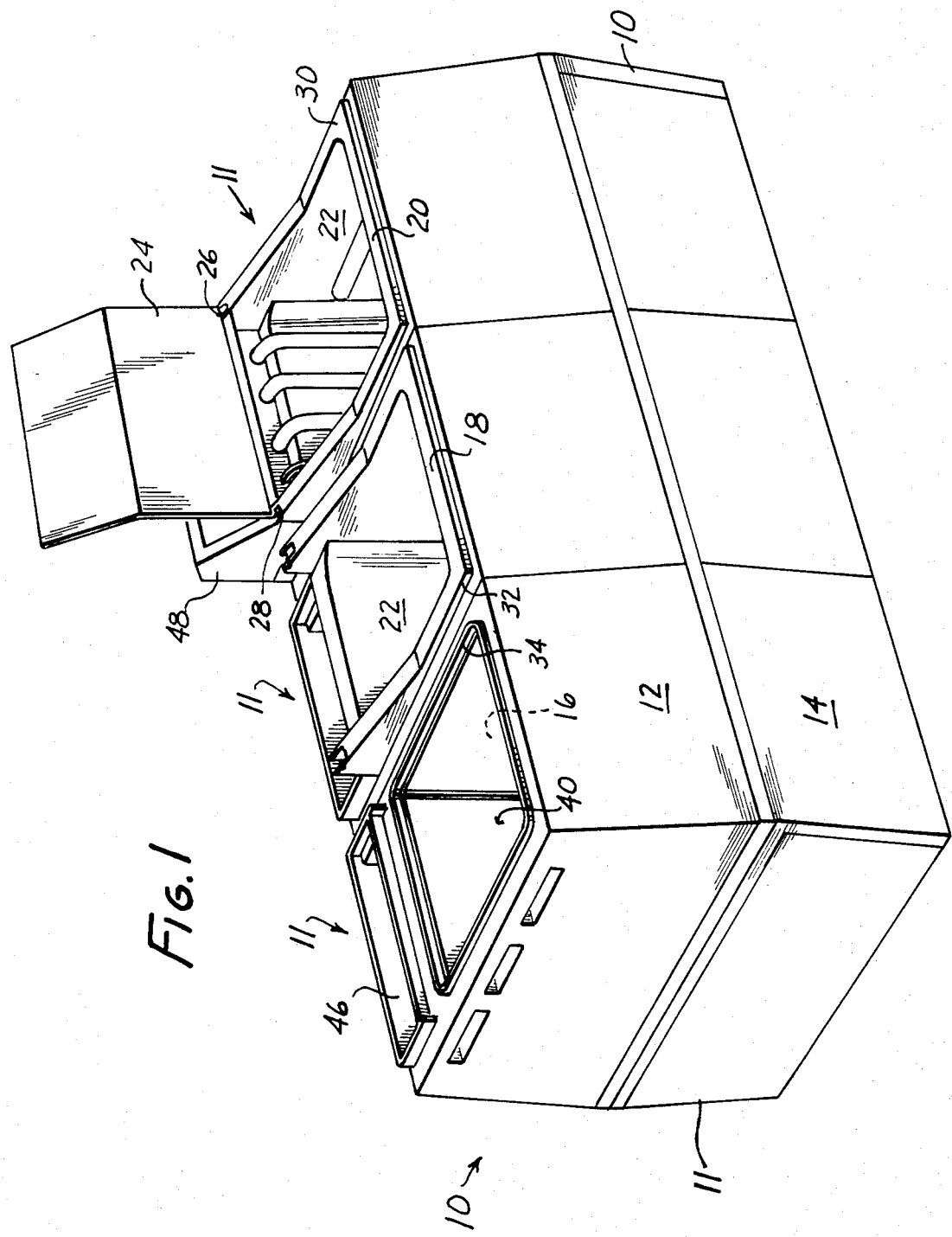

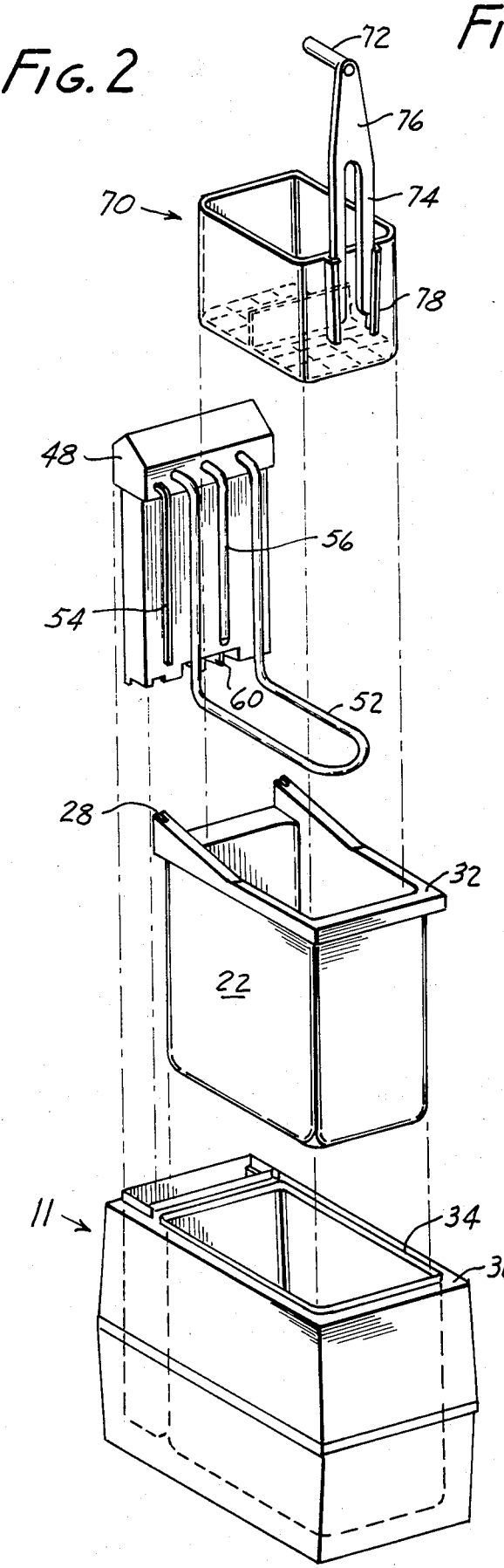
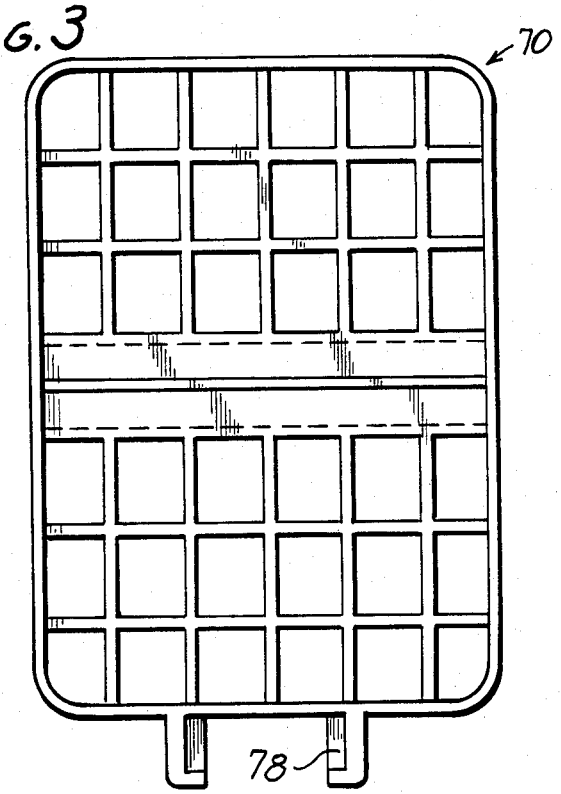
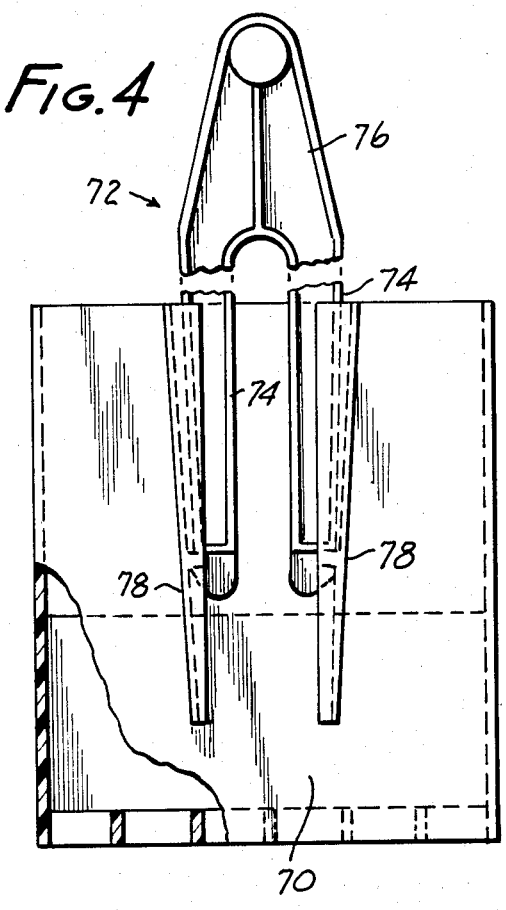

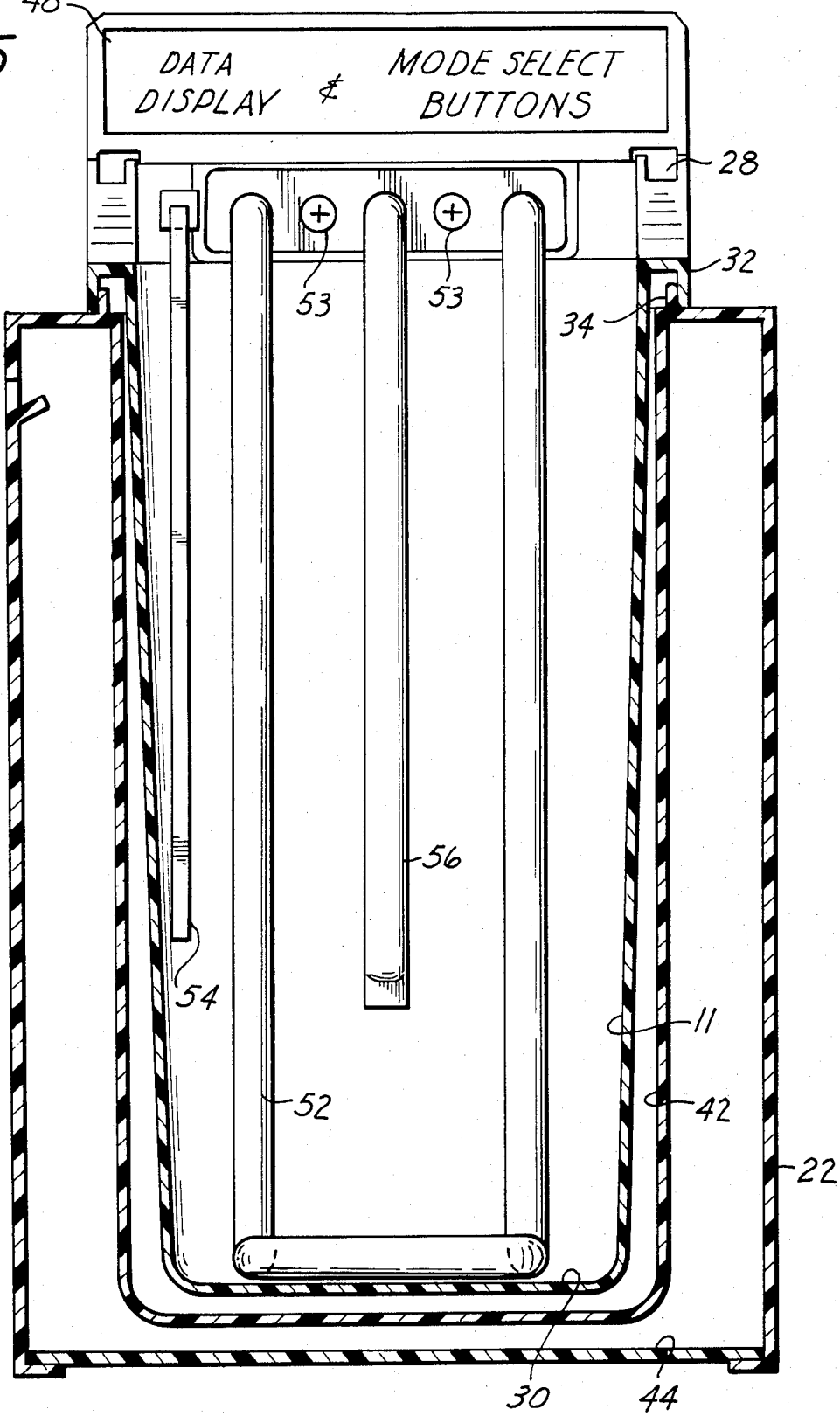

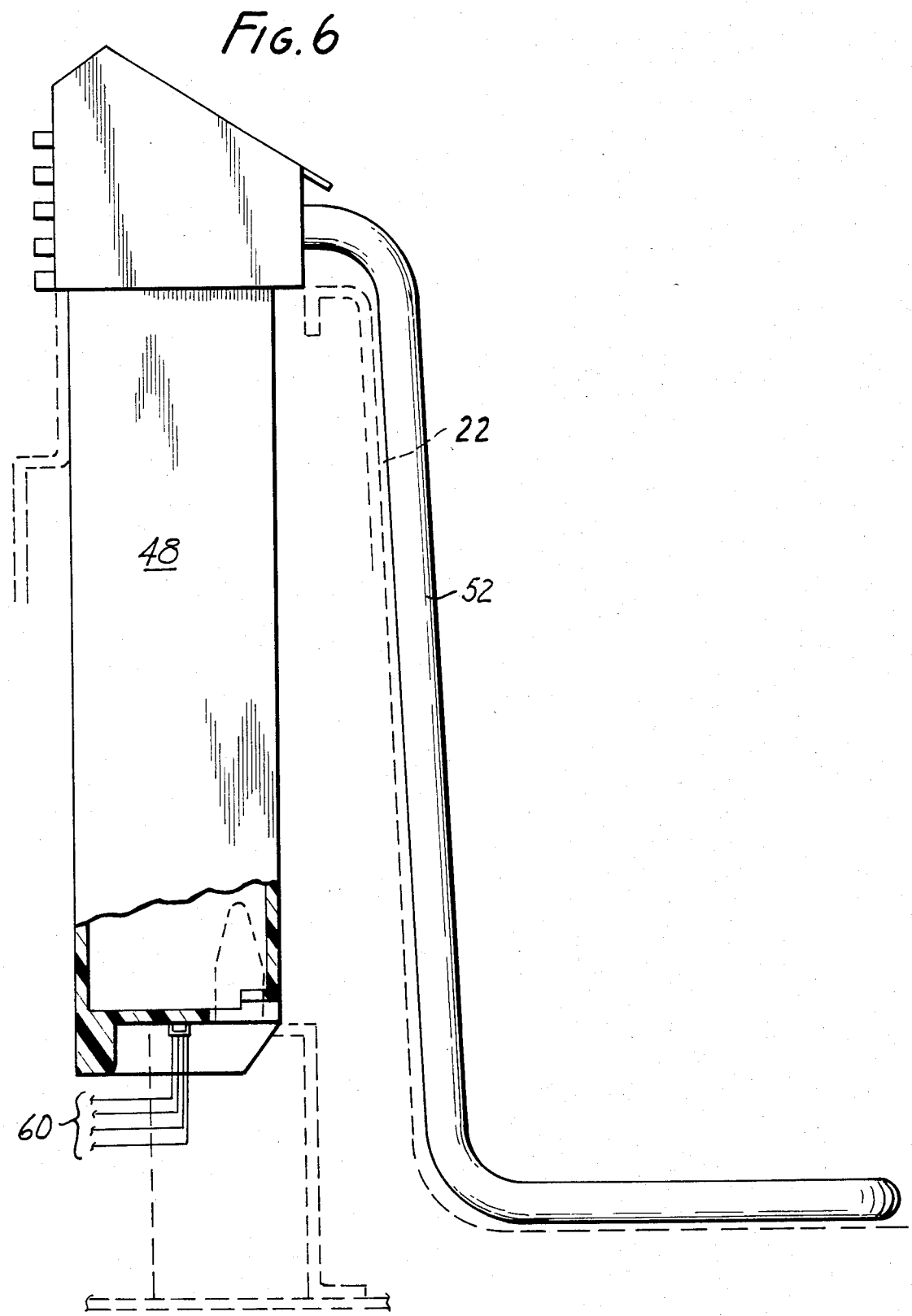

HYDROCOLLOID CONDITIONER APPARATUS

TECHNICAL FIELD

This invention has to do with conditioning of hydrocolloid, the agar-agar based dental materials with which dentists take impressions before making dental prostheses. Such conditioning is accomplished in water baths by first exposing suitably packaged hydrocolloid to a limited, e.g. 10 minute, period boiling water cycle, then storing for up to 5 days at a lower temperature, and finally briefly conditioning just before use to bring the hydrocolloid to a patient-tolerable temperature and to build body in the hydrocolloid. The invention is specifically concerned with improvements in known hydrocolloid conditioning devices to enable automatically commenced and terminated boil cycles, automatic shut-off in the event of low water, ready adjustment of bath temperatures being held, automatic sensing of boil condition in the bath in response to no further increase in water temperature over a defined increment of time, and sequenced commencing and termination of the boil cycle upon such condition being reached independent of the actual boil temperature and thus independent of the altitude at which the device is used, audible signaling of operations, digital read-out of device parameters at all times, immersion heating of the water in each bath for more rapid response, and all in an attractive modular design featuring separable bath tanks, site-specific electrical connections and overrides against accidental boiling, modular bath tank contruction adapted to perform different functions in different installation sites, and removable trays to hold the hydrocolloid packages in the bath tanks, which trays are orientation-reversible to accommodate the several popular sizes of hydrocolloid packaging available to the dentist.

BACKGROUND ART

In U.S. Pat. No. 3,345,497 to Porteous, there is disclosed an electric water bath heater which has been a market success for many years. The disclosure of earlier patent U.S. Pat. No. 3,345,497 is hereby incorporated herein by reference. Despite its outstanding commerical success, many features which the modern practioner would find useful have not been available on the patented device, such as those advantages and features of my new apparatus which are set out above.

DESCRIPTION OF THE INVENTION

In the busy dental office, the prompt availability of properly conditioned hydrocolloid material is essential. The practioner and his assistants, nonetheless should not have to waste time setting timers, watching equipment time through cycles, or guessing about the status of the different temperature baths being used. In addition to these requirements, it still is very important to the dentist that he always have available in his office or laboratory heating apparatus which is ready and in operating condition to do the work required, and thus there is need for modular apparatus in which parts can be replaced readily. Moreover, certain practioners will require less than a full set-up of bath tanks and provision must be made for them to have as many features as possible without having to have a full set-up with multiple baths, preferably while retaining all temperature cycling and maintainence features for serial rather than parallel use.

Thus, it is an object of the present invention to provide a hydrocolloid conditioner of the water bath type, of modular construction and sophisticated signals and controls for maximizing the convenience and utility of the conditioner to the dentist.

It is another object of the present invention to provide such a conditioner in which the modular bath tank units which can be positioned at any one of a plurality of locations and still perform all of the functions required of the unit at any one of the locations, while limiting boil functions to a particular location against inadvertent boiling events.

Another object of the invention is to provide a conditioner of this character adapted to maintain different temperatures in different units of the apparatus in accordance with essential requirements of different materials, functions, or stages of work to be performed.

Other objects and features of the present invention will become apparent hereinafter.

The foregoing objects are realized in accordance with the invention in a hydrocolloid conditioner comprising a frame, a bath tank separably supported by the frame for containing water heated to a pre-determined temperature useful in the conditioning of hydrocolloid material, heating means comprising a power supply and a heating element disposed within the bath, and a microprocessor interfaced with a triac control circuit for turning on and off the heating means responsive to command from the microprocessor. In particular embodiments, the heating element comprises an extended rod means receivable in the bath tank, and a plug body supporting the extended rod means in electrically coupled relation, the frame and plug body defining complementary plug and receptacle structure, whereby the extended rod means is electrically connectible to the power supply by coupling of the plug body to the frame; the bath tank comprises an upwardly openable container having a plurality of upright walls arranged to define a generally rectangular cross-section volume in the tank; a removable rack is provided adapted for immersion within the bath above the heating elements in hydrocolloid carrying relation, as well as handle means for the rack, the rack and handle means defining complementary snap-fit assembly structure; the frame defines a first chamber adapted to snugly receive the plug body in registered relation with the bath tank, and a second chamber defining electrical contact means for electrically connecting the heating elements to the power supply.

In certain embodiments there is provided a plurality of tank bath and corresponding chambers defined by the frame, one only of the chambers defining electrical contact means enabling heating of the heating elements sufficiently to boil water in contact with the elements; the plural bath tanks being supported by the frame in registered relation, and heating means for each the bath tank, a common power supply to the heating means, and plural means sensing the temperature condition in each the bath tank in microprocessor activating relation, whereby water in each of the tanks is temperature regulated and independently of water temperature in the others the baths.

In a particularly preferred embodiment there is provided an apparatus for the preparation of dental hydrocolloid impression material comprising: a first bath tank and means for heating water in the first tank to boiling temperature; first temperature sensing means for sensing the temperature of water in the first bath tank; first heating control means responsive to the first temperature sensing means sensing a boiling condition to cycle water in the first bath through a timed cycle sufficient to condition dental hydrocolloid; and means sensing the presence of water in the first bath tank in heating disabling relation responsive to the absence of water therein.

In this and like embodiments, there is provided in an apparatus for the preparation of dental hydrocolloid impression material a first bath tank and means for heating water in the first bath tank to boiling temperature; a second bath tank and means for heating and holding water in the second bath tank at a predetermined elevated temperature less than water boiling temperature and suitable for long term storage of dental hydrocolloid; a third bath tank and means for heating water in the third bath tank at a predetermined elevated temperature less than that in the second bath tank for immediately bodying the dental hydrocolloid; first temperature sensing means for sensing the temperature of water in the first bath tank; first heating control means responsive to the first temperature sensing means sensing a boiling condition to cycle water in the first bath through a timed cycle sufficient to condition dental hydrocolloid; signal means signalling completion of the timed boiling cycle; second heating control means holding the temperature of water in the second bath tank at an elevated but less than boiling temperature for reception of the conditioned hydrocolloid; means signalling the temperature of the second bath tank; third heating control means holding the temperature of water in the third bath tank at an elevated temperature less than that of the second tank and suitable for rapidly bodying the dental hydrocolloid for use; means for signalling the temperature of the third bath tank; and means sensing the presence of water in the first bath tank in heating disabling relation responsive to the absence of water therein.

In each of the foregoing embodiments there may be included one or more of the following features: at least one of the first, second and third heating means comprises an electrical heating element immersed in the bath tank water; the first heating control means comprises a programmed microprocessor interfaced to a triac control circuit for turning on and off the heating element responsive to commands from the microprocessor; the means for sensing the temperature of the first bath tank water comprises a thermistor immersed therein and linked to an analog-to-digital converter circuit interfaced to the microprocessor to send data regarding the temperature of the water to the microprocessor in digital form; the microprocessor is programmed to maintain a boiling condition in the first tank bath for a pre-set period responsive to receiving temperature data from the bath indicating no rise in temperature for a pre-defined period; the microprocessor is programmed to turn on and off the first heating element respectively to increase the heat in the first bath tank water until the water rises to a temperature substantially equal to a selected temperature of the first bath tank water and to not further increase the heat when the water exceeds the selected temperature; means signalling that the water level in the first bath tank has been reduced below a preselected level, the signalling means comprising a resistive sensor exposed within in the boiling bath and linked to a logic circuit interfaced to the microprocessor to allow the signalling of the condition of the boiling bath liquid being reduced below the preselected level; the microprocessor further comprises a means for producing an audible signal responsive to a command from the microprocessor; and including also means for signalling that the liquid level in the boiling bath has been reduced to a preselected level comprising a resistive sensor exposed to the first bath tank water and linked to a logic circuit interfaced to the microprocessor to allow the signalling of the condition of the boiling bath liquid being reduced below the preselected level; the microprocessor causing the audible signal producing to produce such audible signal responsive to receiving the signalling of the condition of the first bath tank water being reduced below the preselected level from the resistive sensor and logic circuit; and also means for indicating the elapse of a selected time period after the dental hydrocolloid is placed in the third bath tank which may comprise the programmed microprocessor causing the means for producing the audible signal to produce such audible signal after the microprocessor has counted down the selected time period.

THE DRAWING

The invention will be further described as to an illustrative embodiment in accordance with the accompanying drawings in which:

FIG. 1 is a perspective view of the present apparatus;

FIG. 2 is an enlarged detail exploded view of a single module;

FIG. 3 is a top plan view of a hydrocolloid carrying rack according to the invention;

FIG. 4 is a rear elevational view of the rack and handle, partly broken away to show underlying parts;

FIG. 5 is a front elevational view generally in section of the assembled module in place in a bath tank;

FIG. 6 is a side elevational view of the plug body assembled with the frame;

PREFERRED MODES

Figure 7:
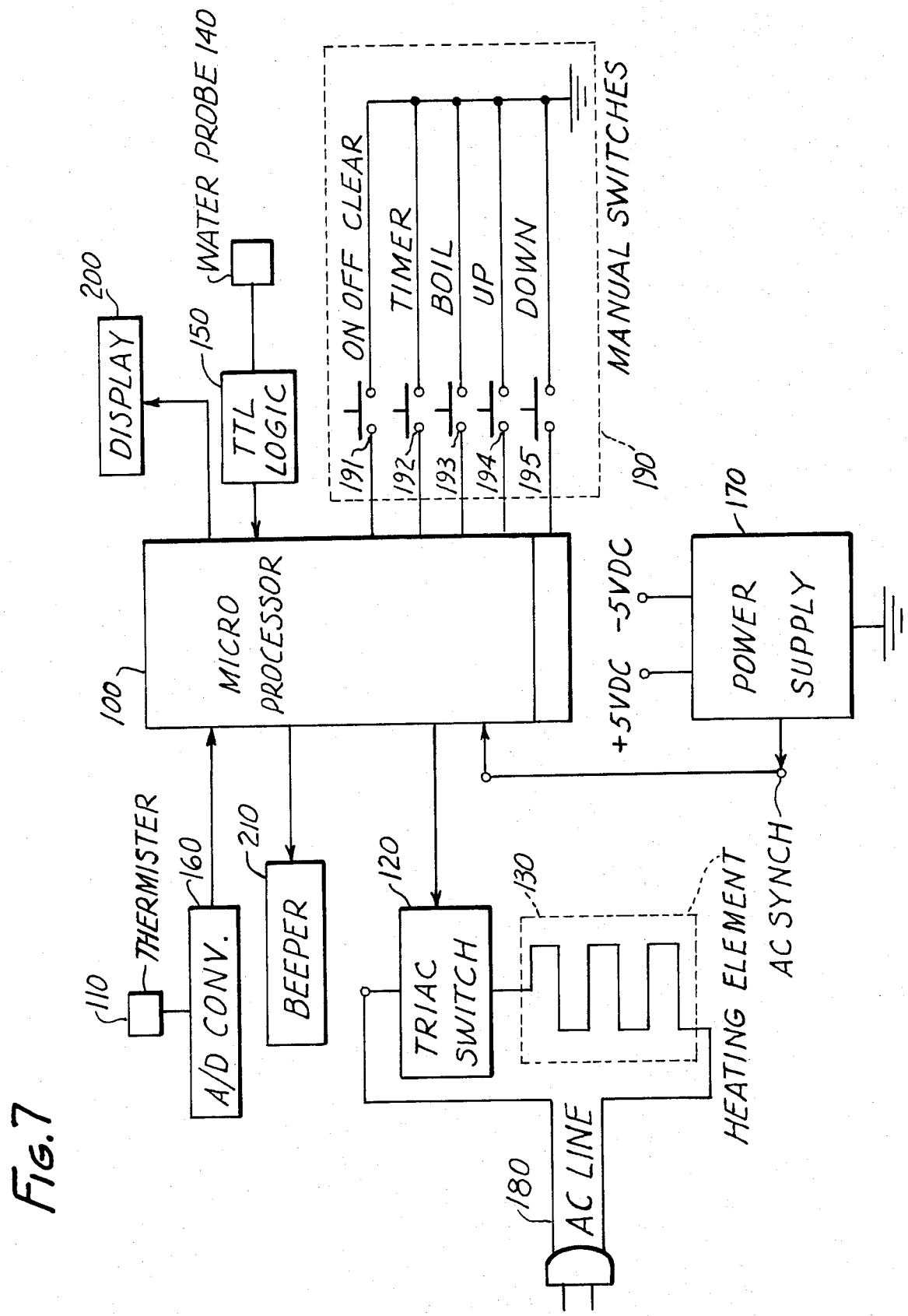
FIG. 7 is an electronic block diagram of the electronic control features of the invention.

The present apparatus offers the dentist the convenience and time-saving advantage of pre-set temperatures in each bath, (which may be overridden up or down the user, but which are pre-set to the usual values of 150° F. in the stoage bath and 110° F. in the tempering bath); accuracy of bath temperature to 1° F.; automatic timer for timing hydrocolloid tempering, pre-set to 5 minutes (but likewise overrideable) and resettable to time gel time in the mouth; countdown display so the dentist is ready when the hydrocolloid is; fault display to signal power outages, OFF condition or low water level in any bath; real time indication of the operating mode: time, temperature and liquefaction; automatic start of boil period upon reaching boil temperature; microcircuitry for reliability; interactive temperature sensing for gradual variation; immersion heaters for rapid results; and audible signals of conditions.

With reference now to the drawing in detail, and first referring to the electronic block diagram contained in FIG. 7, the preferred embodiment of the electronics of the present invention for controlling the boiling bath (tank 16) is shown. The heart of the electronics is the microprocessor 100 which preferrable consists of a PIC 1650A 8-bit microprocessor manufactured by General Instruments. The boiling bath is typically linked to the electronics via (1) a thermistor 110 attached to the boiling bath which gives the microprocessor 100 continual water temperature data through the analog to digital converter circuit 160, (2) a triac switch circuit 120 to enable the microprocessor 100 to selectively turn on and off the heating element 130, and (3) a resistive type water probe 140 attached to the boiling bath and immersed in the boiling bath water at a predetermined level for sensing if the water level in the boiling bath is below the predetermined level and signalling such a condition to the microprocessor 100 through TTL logic circuit 150. The analog to digital converter circuit 160 preferrably consists of a CA 3162 E integrated circuit and components to interface the thermistor 110 to the analog to digital converter circuit 160.

All of the circuits in FIG. 7 are powered by a power supply 170 which typically provides separate +5 and −5 volt supplies and an AC sync pulse for the microprocessor 100 from the AC line 180.

The functions of the boiling bath are controlled by the microprocessor 100 through manual user switches 190. ON/OFF/CLEAR switch 191 preferably turns the microprocessor 100 on and off and clears any ongoing function. TIMER switch 192 activates the timer mode which causes the microprocessor to count down a preselected but re-selectable time period which will show on display 200. When the preselected time period elapses, a beeper 210 (which may be any type which beeps when connected to an electric current) preferably will sound for a pre-set period time to remind the user that the preselected time period is over. The BOIL switch 193 starts the boil cycle in the microprocessor 100. The boil cycle is characterized by the turning on of the heating element 130 via the triac switch 120, the sensing of the temperature of the water in the boiling bath via the thermistor 110 and analog to digital converter circuit 160, and the shutting off of the heating element 130 when the temperature of the water does not increase for a typical time period of one minute. However, the boil cycle could just as well shut off the heating element 130 when the temperature of the water exceeds a preselected temperature and turn on the heating elements 130 when the temperature of the water falls below the preselected temperature, thus, maintaining the water substantially at the preselected temperature. The UP 194 and DOWN 195 switches allow the user to control the time period of the time mode and the temperature of the water in the boiling bath of other than previously set levels.

The microprocessor 100 may also be fitted with means (not shown) which allow it to selectively display the temperature in degrees Fahrenheit or degrees Centigrade and to operate on a 60 Hertz or 50 Hertz AC line 180 at the option of the user.

The apparatus further includes, as shown in FIGS. 1 to 5, a modular assembly of bath tanks and supporting frame, now to be described. In FIGS. 1, 2, 5 and 6, the frame 10 encloses a plurality of plastic molded housings 11, each suitably of interfitting upper and lower halves 12, 14 into which is fitted three bath tanks 16 (omitted in FIG. 1), 18 and 20. The shape of each bath tank 16, 18, 20 is essentially rectangular in cross-section and formed by four upright walls 22, having a removable top 24 shown illustratively at 24 hinged at 26 to bosses 28 formed on the tank wall 22, and closed at the lower end by wall 30. Each tank 16, 18, 20, has an upper horizontal flange 32 which supports the tank on the vertical flange 34 formed on upper wall 36 of the frame 10.

In FIG. 1, the first bath tank 16 is omitted so that the chamber 40 into which the tank fits, typical of all such chambers may be seen. Chamber 40 is defined by interior wall 42 (FIG. 5) of the housing spaced from the housing lower wall 44. A second chamber 46 into which the plug body 48 for each tank is received is defined also by the housing 11, see the center module in FIG. 1 where the bath tank 18 is shown but not its associated plug body, while in the rightmost module both the tank 20 and the plug body 48 are shown.

In the assembled condition of the apparatus each bath tank 16, 18 and 20 is inserted in its respective chamber 40, and the plug bodies 48 are inserted in their respective chambers 46, placing the extended rod immersion heating elements 52 fastened into the plug bodies by screws 53 within the bath tanks 16, 18, 20 for heating water in the tanks. Water is used in the present description and claims as illustrative and any liquid medium serving the function of heating hydrocolloid may be used with or in place of water. The plug bodies 48 further comprise a temperature sensor 54, and a resistive low water sensor 56 connected to the electronics through complementary contacts 60 for purposes explained above.

The hydrocolloid to be conditioned is inserted in one or another bath tank 16, 18 or 20 in a uniquely advantageous rack 70. As best shown in FIGS. 2, 3 and 4, the rack 70 is a basket shaped device of reticulated construction to permit waterflow therethrough while carrying hydrocolloid. Hydrocolloid is supplied in small ampules useful with syringe applicators or large tubes. The dentist may use one or another. The rack 70 may be used with its open end up as shown in FIG. 2 and this is particularly satisfactory where tubes of hydrocolloid are being conditoned. On the other hand where it is desired the rack 70 may be inverted to define a shelf within the bath tank that keeps the mouth trays readily accessible during hydrocolloid conditioning therein.

The handle 72 comprising spring fingers 74 extending from a common terminus 76 snap-fits into combination slide and keeper 78 formed on the rack 70 in either upright or inverted condition of the rack, lending great convenience to either mode of use of the rack.

In use then, hydrocolloid containers are placed first in a rack 70 for immersion in bath tank 16 which is the BOIL bath in the drawing embodiment. The microprocessor is activated by operation of appropriate switches not shown, and full power is applied to the heating element rod 52. The temperature of the BOIL bath and when boiling temperature is reached, the timing of the boil cycle is commenced. This period is preset for ten minutes but may be individually set. Because altitude affects boil temperatures, the microprocessor is programmed to sense no further rise in temperature for a specific period, say one minute, which will be indicative of a boiling condition, while an absolute temperature measurement might indicate not having reached a theoretical boiling temperature. The automatic commencement of the boil cycle eliminates dentist guessing when boiling might have been reached.

After completion of the boil cycle, a beeper sounds and heat is shut down. The hydrocolloid is carried in the same rack 70 to the next bath tank 18 which is a storage bath. There a temperature of 150° F. is maintained which will keep the now liquefied hydrocolloid ready for use for several days.

When use of hydrocolloid is required, the stored material is placed in the tempering bath tank 20. There a temperature of 110° F. is typically maintained to lower the hydrocolloid to a patient tolerable temperature, and to increase the body of the hydrocolloid. Typically it takes 5 minutes to temper, and so, as noted above the tempering bath is preset to beep after five minutes. The same timer feature at bath tank 20 can be used to time gel time in the patient's mouth by resetting as the hydrocolloid is placed in the mouth.

As a further safety feature, although the bath tanks are modular and may be used in any position, the electrical connection 60 in the storage bath and the tempering bath omits the BOIL circuit so that boiling cannot occur in these baths.

There is thus provided a highly advantageous apparatus for the conditioning of hydrocolloid, which automatically takes cares of many of the time related functions of hydrocolloid use, and frees the dental professional for professional duties while ensuring that time critical functions are efficiently accomplished.

I claim:

1. A hydrocolloid conditioner comprising a frame, a bath tank separably supported by said frame for containing water heated to a pre-determined temperature useful in the conditioning of hydrocolloid material, heating means comprising a power supply and a heating element disposed within the bath, and a microprocessor interfaced with a triac control circuit for turning on and off said heating means responsive to command from said microprocessor.

2. The hydrocolloid conditioner according to claim 1, in which said heating element comprises an extended rod means receivable in said bath tank, and a plug body supporting said extended rod means in electrically coupled relation, said frame and plug body defining complementary plug and receptacle structure, whereby said extended rod means is electrically connectible to said power supply by coupling of said plug body to said frame.

3. The hydrocolloid conditioner according to claim 1, in which said bath tank comprises an upwardly openable container having a plurality of upright walls arranged to define a generally rectangular cross-section volume in said tank.

4. The hydrocolloid conditioner according to claim 1, including also a removable rack adapted for immersion within said bath above said heating elements in hydrocolloid carrying relation.

5. The hydrocolloid conditioner according to claim 4, including also handle means for said rack, said rack and handle means defining complementary snap-fit assembly structure.

6. The hydrocolloid conditioner according to claim 1, in which said frame defines a first chamber adapted to snugly receive said plug body in registered relation with said bath tank, said second chamber defining electrical contact means for electrically connecting said heating elements to said power.

7. The hydrocolloid conditioner according to claim 6, in which there is a plurality of tank bath and corresponding chambers defined by said frame, one only of said chambers defining electrical contact means enabling heating of said heating elements sufficiently to boil water in contact with said elements.

8. The hydrocolloid conditioner according to claim 1, including also plural bath tanks supported by said frame in registered relation, heating means for each said bath tank, a common power supply to said heating means, plural means sensing the temperature condition in each said bath tank in microprocessor activating relation, whereby water in each of said tanks is temperature regulated and independently of water temperature in the others said baths.

9. An apparatus for the preparation of dental hydrocolloid impression material comprising;
a first bath tank and means for heating water in said first bath tank to boiling temperature;
first temperature sensing means for sensing the temperature of water in said first bath tank; and,
first heating control means responsive to said first temperature sensing means sensing a boiling condition to cycle water in said first through a timed cycle sufficient to condition dental hydrocolloid;
said control means sensing no rise in temperature for a period as said boiling condition.

10. An apparatus for the preparation of dental hydrocolloid impression material comprising:
a first bath tank and means for heating water in said first bath tank to boiling temperature;
a second bath tank and means for heating and holding water in said second bath tank at a predetermined elevated temperature less than water boiling temperature and suitable for long term storage of dental hydrocolloid;
a third bath tank and means for heating water in said third bath tank at a predetermined elevated temperature less than that in said second bath tank for immediately bodying the dental hydrocolloid;
first temperature sensing means for sensing the temperature of water in said first bath tank;
first heating control means responsive to said first temperature sensing means sensing a boiling condition to cycle water in said first bath through a timed cycle sufficient to condition dental hydrocolloid;
signal means signalling completion of the timed boiling cycle;
second heating control means holding temperature of water in said second bath tank at an elevated but less than boiling temperature for reception of the conditioned hydrocolloid;
means signalling the temperature of the second bath tank;
third heating control means holding the temperature of water in the third bath tank at an elevated temperature less than that of the second tank and suitable for rapidly bodying the dental hydrocolloid for use;
means for signalling the temperature of the third bath tank;
and means sensing the presence of water in said first bath tank in heating disabling relation responsive to the absence of water therein.

11. The apparatus according to claim 10, in which at least one of said first, second and third heating means comprises an electrical heating element immersed in the bath tank water.

12. The apparatus according to claim 10, in which said first heating control means comprises a programmed microprocessor interfaced to a triac control circuit for turning on and off the heating element responsive to commands from the microprocessor.

13. The apparatus according to claim 12, in which the means for sensing the temperature of said first bath tank water comprises a thermistor immersed therein and linked to an analog-to-digital converter circuit interfaced to the microprocessor to send data regarding the temperature of the water to the microprocessor in digital form.

14. The apparatus according to claim 13, in which said microprocessor is programmed to maintain a boiling condition in the first tank bath for a pre-set period responsive to receiving temperature data from the bath indicating no rise in temperature for a pre-defined period.

15. The apparatus according to claim 14, in which said microprocessor is programmed to turn on and off said first heating element to increase the heat in said first bath tank water until the water rises to a temperature substantially equal to a selected temperature of the first bath tank water and to not further increase said heat when said water exceeds the selected temperature.

16. The apparatus according to claim 15, including also means signalling that the water level in said first bath tank has been reduced below a preselected level, said signalling means comprising a resistive sensor exposed within in the boiling bath and and linked to a logic circuit interfaced to the microprocessor to allow the signalling of the condition of the boiling bath liquid being reduced below the preselected level.

17. The apparatus according to claim 10 in which said microprocessor further comprises a means for producing an audible signal responsive to a command from the microprocessor; and including also means for signalling that the liquid level in the boiling bath has been reduced to a preselected level comprising a resistive sensor exposed to the first bath tank water and linked to a logic circuit interfaced to the microprocessor to allow the signalling of the level of the boiling bath liquid being reduced below the preselected level; said microprocessor causing said audible signal producing to produce such audible signal responsive to receiving the signalling of the condition of the first bath tank water being reduced below the preselected level from the resistive sensor and logic circuit.

18. The apparatus according to claim 10, including also means for indicating the elapse of a selected time period after the dental hydrocolloid is placed in said third bath tank.

19. The apparatus according to claim 18, in which the means for indicating the elapse of a selected time period after the dental hydrocolloid is placed in said third bath tank comprises said programmed microprocessor causing the means for producing the audible signal to produce such audible signal after the microprocessor has counted down the selected time period.

* * * * *